Dec. 18, 1956 E. S. BOERNER Plant Pat. 1,540
ROSE PLANT
Filed Jan. 5, 1956
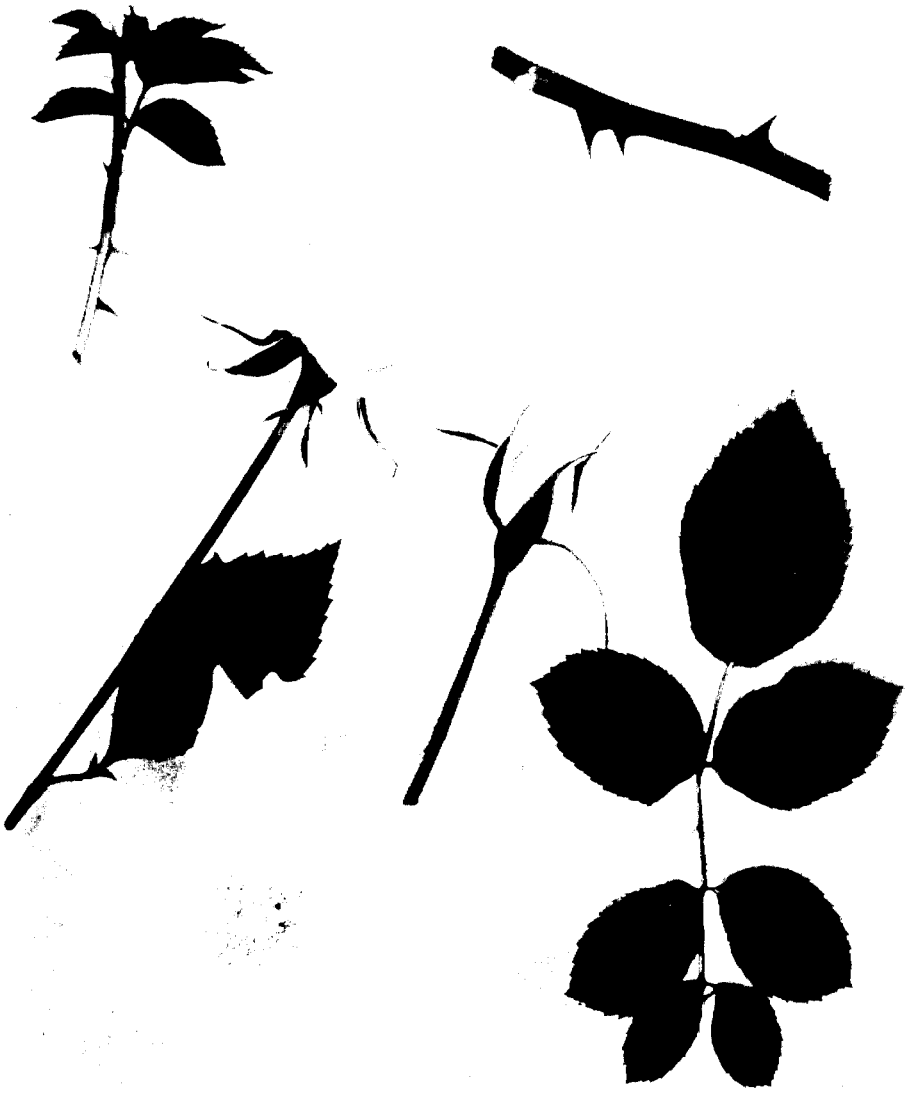
Inventor.
E. S. Boerner
By: Robb & Robb
Attorneys.

United States Patent Office

Plant Pat. 1,540
Patented Dec. 18, 1956

1,540

ROSE PLANT

Eugene S. Boerner, Newark, N. Y., assignor to Jackson & Perkins Company, Newark, N. Y., a corporation of New York Application January 5, 1956, Serial No. 557,619

1 Claim. (Cl. 47—61)

The present invention relates to a new and distinct variety of rose plant of the large-flowered polyantha class, which was originated by me by crossing an unnamed and unpatented Orange seedling with the well-known rose variety "Demure" (Plant Patent No. 1,065).

The primary obective of this breeding was to produce a new rose variety which bears White flowers of long-lasting quality and having very stiff petals. This objective was fully achieved, along with other desirable features which are particularly unique in combination, as evidenced by the following outstanding characteristics which are notable in the new variety:

(1) The free flowering habit;

(2) The very stiff petals and long-lasting quality of the flowers; and (3) The colorful effect attributed to the long-lasting White flowers and the rich foliage, thus making the new variety particularly useful and desirable for out-of-door decoration.

Asexual reproduction of the new variety by budding, as performed at Newark, New York, and also at Pleasanton, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert Ridgway's Color Standards and Nomenclature:

Parentage: Seedling.
*Seed parent.*—An unnamed Orange seedling.
*Pollen parent.*—"Demure."

Classification:
*Botanic.*—Large-flowered polyantha.
*Commercial.*—Floribunda.

FLOWER (Observations made from specimens grown in a greenhouse at Newark, New York, in the early part of April and in the late morning.)

Blooming Habit: Recurrent—continuous.

Bud:
*Size.*—Medium.
*Form.*—Long; pointed; is not affected by wet or hot weather.
*Color.*—When sepals first divide—Light Viridine Yellow, Plate 5. When petals begin to unfurl—Pale Dull Green Yellow, Plate 17. When half-blown: Inside of petals—White, Plate 53, lightly overcast with Marguerite Yellow, Plate 30; reverse of petals—White, Plate 53, lightly overcast with Sea-foam Yellow, Plate 31.
*Sepals.*—Slightly branched; curl back when petals begin to unfurl. Color—inside—Kildare Green, Plate 31; outside—Biscay Green, Plate 17.
*Calyx.*—Color—Biscay Green, Plate 17. Shape—pear. Size — small. Aspect — smooth. Odor when rubbed—none.
*Peduncle.*—Length — medium. Aspect — rough. Strength—erect; slender. Color—Absinthe Green, Plate 31.
*Opening.*—Opens up well; is not affected by adverse weather conditions.

Bloom:
*Size.* — Medium. Average size when fully expanded—from 2½ inches to 3 inches.
*Borne.*—Several together.
*Stems.*—Medium length; strong.
*Form (when first open).*—Flat. Permanence—outer petals curl back.
*Petalage.*—Double (full but open center). Number of petals under normal conditions—35.
*Color.*—Center of flower—White, Plate 53, lightly overcast with Marguerite Yellow, Plate 30. Outer petals—White, Plate 53. Base of petals (aiglet)—Pale Cendre Green, Plate 6. Inside of petals—White, Plate 53. Reverse of petals—White, Plate 53. General tonality from a distance—White, Plate 53.
*Discoloration.*—General tonality at end of first day—White, Plate 53, lightly overcast with Marguerite Yellow, Plate 30. Second day—White, Plate 53. Third day—White, Plate 53.

Petals:
*Texture.*—Leathery; is not affected by wet or hot weather.
*Appearance.*—Inside—satiny; outside—shiny.
*Form.*—Oval; slightly notched.
*Arrangement.* — Imbricated (regularly arranged shingle-like).
*Petaloids in Center.*—Few; small.
*Persistence.*—Drop off cleanly.
*Fragrance.*—Slight. Nature—tea (average hybrid tea scent).
*Lasting quality.*—On the plant—very long. As cut flower—very long.

GENITAL ORGANS

Stamens, anthers: Medium size; many; regularly arranged around styles. Color—Deep Colonial Buff, Plate 30.
Stamens, filaments (threads): Medium length. Color—Marguerite Yellow, Plate 30.
Pollen: Color—Ivory Yellow, Plate 30.
Styles: Columnar; uneven lengths; medium length; thin.
Stigmas: Color—Primrose Yellow, Plate 30.
Ovaries: All enclosed in calyx.
Hips: None.
Seeds: None.

PLANT

Form: Bush.
Growth: Vigorous; upright.
Foliage: Compound of 5 to 7 leaflets.
*Size.*—Large.
*Quantity.*—Normal.
*Color.*—New foliage: Upper side—Morocco Red, Plate 1, with center lightly overcast with Yellowish Oil Green, Plate 5; under side—Oxblood Red, Plate 1. Old foliage: Upper side—Yew Green, Plate 31; under side—Light Cress Green, Plate 31.
*Shape.*—Oval pointed.
*Texture.*—Upper side—leathery; under side—smooth.
*Ribs and veins.*—Ordinary.
*Edge.*—Serrated (saw-toothed).
*Serration.*—Both double and single; sharp.

*Leaf stem.*—Color—Absinthe Green, Plate 31. Under side—prickles.

*Stipules.*—Medium length; slightly bearded.

Wood:

*New wood.*—Color—Garnet Brown, Plate 1. Bark—smooth.

*Old wood.*—Color—Cress Green, Plate 31. Bark—smooth.

Thorns:

*Thorns.*—Quantity: On main stalks from base—ordinary; on laterals from stalk—ordinary. Form—narrow base; medium length; straight. Color (when young)—Carmine, Plate 1. Position—Irregular.

*Prickles.*—Quantity: On main stalks—none; on laterals—none.

*Short needles.*—Quantity: On main stalks—none; on laterals—none.

I claim:

A new and distinct variety of rose plant of the large-flowered polyantha class, substantially as herein shown and described, characterized particularly as to novelty by its free flowering habit, the very stiff petals and long-lasting quality of its flowers, and the colorful effect attributed to its long-lasting White flowers and rich foliage, with attending suitability for out-of-door decoration.

No references cited.